United States Patent
Kishimoto et al.

(10) Patent No.: US 9,162,945 B2
(45) Date of Patent: *Oct. 20, 2015

(54) PROCESS FOR PREPARING 2-CHLORO-3,3,3-TRIFLUOROPROPENE

(71) Applicant: DAIKIN INDUSTRIES, LTD., Osaka (JP)

(72) Inventors: Masayuki Kishimoto, Osaka (JP); Yuzo Komatsu, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/379,044

(22) PCT Filed: Mar. 21, 2013

(86) PCT No.: PCT/JP2013/059161
§ 371 (c)(1),
(2) Date: Aug. 15, 2014

(87) PCT Pub. No.: WO2013/141409
PCT Pub. Date: Sep. 26, 2013

(65) Prior Publication Data
US 2015/0057473 A1    Feb. 26, 2015

Related U.S. Application Data

(60) Provisional application No. 61/614,102, filed on Mar. 22, 2012.

(51) Int. Cl.
C07C 17/20    (2006.01)
C07C 17/25    (2006.01)

(52) U.S. Cl.
CPC ............... *C07C 17/206* (2013.01); *C07C 17/25* (2013.01)

(58) Field of Classification Search
CPC ............................... C07C 17/25; C07C 17/206
See application file for complete search history.

(56) References Cited

U.S. PATENT DOCUMENTS

| | | | |
|---|---|---|---|
| 8,058,486 B2 | 11/2011 | Merkel et al. | |
| 2007/0197842 A1* | 8/2007 | Mukhopadhyay et al. | ... 570/155 |
| 2009/0030247 A1 | 1/2009 | Johnson et al. | |
| 2009/0240090 A1 | 9/2009 | Merkel et al. | |
| 2011/0105807 A1* | 5/2011 | Kopkalli et al. | ............... 570/155 |
| 2011/0155942 A1 | 6/2011 | Pigamo et al. | |
| 2011/0207975 A9 | 8/2011 | Merkel et al. | |
| 2012/0078020 A1* | 3/2012 | Elsheikh et al. | ............... 570/160 |
| 2012/0178977 A1 | 7/2012 | Merkel et al. | |
| 2014/0256995 A1 | 9/2014 | Wang et al. | |

FOREIGN PATENT DOCUMENTS

| | | |
|---|---|---|
| JP | 2009-227675 | 10/2009 |
| JP | 2014-530214 | 11/2014 |
| WO | 2007/079431 | 7/2007 |
| WO | 2008/054781 | 5/2008 |
| WO | 2009/003084 | 12/2008 |
| WO | 2009/015317 | 1/2009 |
| WO | 2010/123148 | 10/2010 |
| WO | 2013/065617 | 5/2013 |

OTHER PUBLICATIONS

International Search Report issued Jul. 19, 2013 in International (PCT) Application No. PCT/JP2013/059161 along with the Written Opinion.

* cited by examiner

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

Provided is a process for preparing 2-chloro-3,3,3-trifluoropropene, wherein at least one chlorine-containing compound selected from the group consisting of chloropropane represented by formula (1): $CX_3CHClCH_2Cl$, wherein each X is the same or different and each represents Cl or F, chloropropene represented by formula (2): $CClY_2CCl=CH_2$, wherein each Y is the same or different and each represents Cl or F, and chloropropene represented by formula (3): $CZ_2=CClCH_2Cl$, wherein each Z is the same or different and each represents Cl or F, is used as a starting compound, and said at least one chlorine-containing compound is reacted with hydrogen fluoride while being heated in a gaseous state in the presence of 50 ppm or more of water relative to the chlorine-containing compound. The process of the present invention makes it possible to produce 2-chloro-3,3,3-trifluoropropene (HCFO-1233xf) in a manner that is easily conducted, economically advantageous, and suitable for industrial scale production.

4 Claims, No Drawings

PROCESS FOR PREPARING 2-CHLORO-3,3,3-TRIFLUOROPROPENE

TECHNICAL FIELD

The present invention relates to a process for preparing 2-chloro-3,3,3-trifluoropropene.

BACKGROUND ART

2-Chloro-3,3,3-trifluoropropene (HCFO-1233xf) represented by the chemical formula: $CF_3CCl=CH_2$ is a compound that is useful as an intermediate for producing various kinds of fluorocarbons, and also as a monomer component of various kinds of polymers.

A known process for preparing HCFO-1233xf comprises reacting some material with anhydrous hydrogen fluoride (HF) in a gas phase in the presence of a catalyst. For example, Patent Literature (PTL) 1 listed below discloses a process comprising fluorination of 1,1,2,3-tetrachloropropene (HCO-1230xa, $CCl_2=CClCH_2Cl$) in a gas phase using a chromium-based catalyst. Patent Literature 2 listed below also reports a process comprising fluorination of 1,1,2,3-tetrachloropropene in a gas phase using a chromium-based catalyst. Further, Patent Literature 3 teaches that 1,1,2,3-tetrachloropropene (HCO-1230xa), 1,1,1,2,3-pentachloropropane (HCC-240db), 2,3,3,3-tetrachloropropene (HCO-1230xf), etc., can be fluorinated in the presence of a stabilizer for minimizing catalyst deterioration.

However, the processes disclosed in the above literature have various disadvantages. For example, further improvement in the yield of HCFO-1233xf is required, use of a catalyst is costly, and many products are produced by the reaction in addition to the target product of HCFO-1233xf, resulting in unsatisfactory selectivity. Further, since catalytic activity tends to decrease as a reaction proceeds, there have been many attempts to use a stabilizer for the purpose of minimizing catalyst deactivation.

Patent Literature 4 discloses a process comprising reacting 1,1,2,3-tetrachloropropene (HCO-1230xa) with anhydrous hydrogen fluoride (HF) in a liquid phase in the presence of a halogenated antimony catalyst. However, this process is unsuitable for industrial production, because handling the catalyst is difficult, the process is uneconomical due to the occurrence of reactor corrosion, necessity for waste treatment, etc., and its operation is problematic.

Patent Literature 5 reports that HCFO-1233xf can be prepared by reacting 1,1,2-tetrachloropropene (HCO-1230xa) with anhydrous hydrogen fluoride (HF) in a liquid phase in the absence of a catalyst. However, this process is not suitable for industrial-scale production because a longer reaction time is required as a result of its low reaction rate, an overly large amount of HF is necessary, severe reaction conditions under high pressure are necessitated, etc.

As described above, a process by which HCFO-1233xf is easily and economically prepared at a high yield has not yet been established.

CITATION LIST

Patent Literature

PTL 1: WO2007/079431 A2
PTL 2: WO2008/054781 A1
PTL 3: WO2009/015317 A1
PTL 4: US2009/0030247 A1
PTL 5: WO2009/003084 A1

SUMMARY OF INVENTION

Technical Problem

The present invention has been accomplished in view of the current status of the foregoing prior art. The main object of the present invention is to provide a process capable of effectively preparing 2-chloro-3,3,3-trifluoropropene (HCFO-1233xf) in a manner easily conducted, economically advantageous, and suitable for industrial scale production.

Solution to Problem

The present inventors conducted extensive research to achieve the above object. As a result, the present inventors found the following. That is, in a process for preparing HCFO-1233xf wherein a chloropropane or chloropropene compound represented by a specific formula is used as a starting material and is subjected to a reaction with hydrogen fluoride while being heated in a gas phase, when the water in the reaction system exceeds a certain amount, the selectivity of the target HCFO-1233xf improves, and the target HCFO-1233xf can be efficiently produced in a single reaction step within a relatively short reaction time. This process makes it possible to eliminate the drawbacks of known preparation processes of HCFO-1233xf. Thus, the process enables the production of HCFO-1233xf in a highly productive manner on an industrial scale. The present invention has been accomplished in view of the above findings.

Specifically, the present invention provides a process for preparing 2-chloro-3,3,3-trifluoropropene as follows.

Item 1. A process for preparing 2-chloro-3,3,3-trifluoropropene comprising:

reacting a chlorine-containing compound with hydrogen fluoride while being heated in a gaseous state in the presence of 50 ppm or more of water relative to the total weight of the chlorine-containing compound, the chlorine-containing compound being at least one compound selected from the group consisting of chloropropane represented by formula (1): $CX_3CHClCH_2Cl$, wherein each X is the same or different and each represents Cl or F; chloropropene represented by formula (2): $CClY_2CCl=CH_2$, wherein each Y is the same or different and each represents Cl or F; and chloropropene represented by formula (3): $CZ_2=CClCH_2Cl$, wherein each Z is the same or different and each represents Cl or F.

Item 2. The process according to Item 1, wherein the reaction is conducted in the absence of a catalyst.

Item 3. The process for preparing 2-chloro-3,3,3-trifluoropropene according to Item 1 or 2, wherein the hydrogen fluoride is used in an amount of 5 to 30 mol relative to 1 mol of the chlorine-containing compound used as a starting material, and the reaction is carried out at 300 to 500° C.

Hereinafter, the process for preparing 2-chloro-3,3,3-trifluoropropene of the present invention is described in more detail.

(1) Starting Compound

In the present invention, at least one chlorine-containing compound selected from the group consisting of chloropropane represented by formula (1): $CX_3CHClCH_2Cl$, wherein each X is the same or different and each represents Cl or F, chloropropene represented by formula (2): $CClY_2CCl=CH_2$, wherein each Y is the same or different and each represents Cl or F, and chloropropene represented by formula (3): $CZ_2=CClCH_2Cl$, wherein each Z is the same or different and each represents Cl or F, is used as a starting compound. By subjecting the chlorine-containing compound used as a starting material to a reaction with hydrogen fluoride under the conditions described below, target 2-chloro-3,3,3-trifluoropropene (HCFO-1233xf) can be prepared in a single reaction step at a high yield.

Of the aforementioned starting compounds, specific examples of chloropropane represented by formula (1): $CX_3CHClCH_2Cl$ include $CCl_3CHClCH_2Cl$ (HCC-240db, bp. 179° C./760 mmHg, 51 to 53° C./3 mmHg), $CFCl_2CHClCH_2Cl$ (HCFC-241db, bp. 157° C.), $CF_2ClCHClCH_2Cl$ (HCFC-242dc, bp. 113 to 114° C.), $CF_3CHClCH_2Cl$ (HCFC-243db), and the like; specific examples of chloropropene represented by formula (2): $CClY_2CCl=CH_2$ include $CCl_3CCl=CH_2$ (HCO-1230xf, bp. 128° C.), $CFCl_2CCl=CH_2$ (HCFO-1231xf, bp. 98.5 to 99° C.), $CF_2ClCCl=CH_2$ (HCFO-1232xf, bp. 57 to 58° C.), and the like; and specific examples of chloropropene represented by formula (3): $CZ_2=CClCH_2Cl$ include $CCl_2=CClCH_2Cl$ (HCO-1230xa, bp. 138° C.), $CFCl=CClCH_2Cl$ (HCFO-1231xb), $CF_2=CClCH_2Cl$ (HCFO-1232xc), and the like.

Of the above starting compounds, HCC-240db ($CCl_3CHClCH_2Cl$ (1,1,1,2,3-pentachloropropane)), HCFC-243db ($CF_3CHClCH_2Cl$ (2,3-dichloro-1,1,1-trifluoropropane)), HCO-1230xf ($CCl_3CCl=CH_2$ (2,3,3,3-tetrachloropropene)), and HCO-1230xa ($CCl_2=CClCH_2Cl$ (1,1,2,3-tetrachloropropene)) are particularly advantageous starting compounds, because these compounds are easily obtainable and inexpensive.

In the present invention, the aforementioned starting compounds can be used singly or in a combination of two or more.

(2) Reaction Method

The preparation process of the present invention comprises reacting an aforementioned starting compound with hydrogen fluoride in a gaseous state while being heated in the presence of 50 ppm or more of water relative to the total weight of the chlorine-containing compound (i.e., starting compound).

By reacting the aforementioned starting compound with hydrogen fluoride under the conditions mentioned above, the selectivity of the target 2-chloro-3,3,3-trifluoropropene (HCFO-1233xf) improves and 2-chloro-3,3,3-trifluoropropene (HCFO-1233xf) can be efficiently produced in a single reaction step.

In the preparation process of the present invention, it is necessary for the aforementioned starting compound to undergo a reaction with hydrogen fluoride in a gaseous state. The starting compound may, however, be in a liquid state at the time of supply, insofar as the starting compound is in a gaseous state when brought into contact with hydrogen fluoride in the reaction temperature region mentioned below. For example, if the starting compound is liquid at normal temperature under normal pressure, the starting compound is evaporated with an evaporator (evaporation region) and is subsequently allowed to pass through a preheating region to be supplied to a mixing region where it is brought into contact with anhydrous hydrogen fluoride. This enables the reaction to be carried out in a gaseous state. The reaction may also be carried out by supplying the starting compound in a liquid state to a reactor, and evaporating the compound when the compound enters the reaction region where it reacts with hydrogen fluoride. There is no limitation to the method for evaporating the starting compound in the reaction region. The starting compound may be evaporated into a gaseous state by, for example, filling a reaction tube with a material that exhibits excellent thermal conductivity, exerts no catalytic activity in the reaction of the present invention, and is stable with respect to hydrogen fluoride, such as nickel beads, Hastelloy pellets, or the like, so as to homogenize the temperature distribution within the reaction tube, heating the reaction tube to not less than the evaporation temperature of the starting compound, and supplying the starting compound in a liquid state.

Hydrogen fluoride is usually fed to the reactor in a gaseous state with the starting compound. The amount of hydrogen fluoride supplied is generally about 3 mol or more, preferably about 5 to 100 mol, and more preferably about 5 to 30 mol, per 1 mol of the starting compound. By setting the use amount within such a range, both the conversion rate of the starting compound and the selectivity of HCFO-1233xf can be maintained within a desirable range. In particular, by supplying 10 mol or more hydrogen fluoride relative to 1 mol of starting compound, the selectivity of HCFO-1233xf can be made extremely high.

The aforementioned starting material may be fed to the reactor as is, or may be diluted with an inert gas, such as nitrogen, helium, argon, or the like, to be fed to the reactor.

In the present invention, the amount of water in the reaction system means the amount of water that is present in the portion where the reaction proceeds in the reactor when the starting compound reacts with hydrogen fluoride within the reaction temperature region mentioned below. More specifically, the amount of water includes, in addition to water contained in the chlorine-containing compound used as a starting material and hydrogen fluoride, the amount of water contained in an inert gas or the like that is a component optionally added, and the amount of water separately added if necessary.

The method for supplying water is not limited, and various methods can be employed. Examples thereof include a method wherein a chlorine-containing compound used as a starting material containing water is supplied to the reactor; anhydrous hydrogen fluoride is made to contain water in advance and then supplied to the reactor; water is supplied using a line separate from one for supplying the starting material; and an inert gas is supplied to the reactor together with vapor.

The water content in the reaction system is preferably about 50 ppm or more, more preferably about 100 ppm or more, still more preferably about 200 ppm or more, and particularly preferably 1,000 ppm or more relative to the total weight of the chlorine-containing compound used as the starting material. The upper limit of water content is not particularly limited. About 10,000 ppm (1% by weight) relative to the total weight of the chlorine-containing compound used as the starting material is preferable to obtain the target product with high selectivity. However, when water content exceeds the above value, facility corrosion or complicated separation of water from the target product may not be avoided.

In the present invention, a starting compound may be reacted with hydrogen fluoride in the presence or in the absence of a catalyst. There is no particular limitation to the types of catalyst used, and various known catalysts for fluorination reaction may be used.

In the present invention, the reaction is preferably conducted in the absence of a catalyst. By carrying out the reaction in the absence of a catalyst, under the conditions described above, and in the presence of water in an amount of at least a certain level, 2-chloro-3,3,3-trifluoropropene can be produced with high selectivity.

There is no limitation to the form of the reactor used in the process of the present invention. When the reaction is conducted in the presence of a catalyst, for example, a tubular flow reactor packed with a catalyst may be used. When the reaction is conducted in the absence of a catalyst, examples of usable reactors include a hollow adiabatic reactor, an adiabatic reactor packed with a porous or nonporous metal or medium that improves the gas-phase mixing state between hydrogen fluoride and the starting material. Also usable is a multitubular reactor in which a heat transmitting medium is used to cool the reactor and to homogenize the temperature distribution within the reactor. When a hollow reactor is used, in a method wherein a reaction tube having a smaller inner diameter is used to improve heat transfer efficiency, it is preferable, for example, that the relationship between the flow rate of the starting material and the inner diameter of the reaction tube be adjusted so that a high linear velocity and a large heat transfer area can be obtained.

It is preferable that the reactor be formed of a material, such as HASTELLOY®, INCONEL®, MONEL®, or INCOLLOY®, that is resistant to the corrosive action of hydrogen fluoride.

In the process of the present invention, the temperature in the reactor is generally about 250 to 600° C., preferably about 300 to 500° C., and more preferably about 350 to 450° C. When the temperature exceeds the upper limit of this temperature range, the selectivity of HCFO-1233xf will be undesirably reduced, but an unduly low temperature decreases the conversion rate of the starting compound. Therefore, unduly high and low temperatures are both undesirable. Performing the reaction at a temperature higher than 450° C. may cause carbide to be produced and adhere to or be deposited on the reaction tube wall or filler, which gradually clogs the inside of the reaction tube. In this case, the carbide residue in the reaction tube may be removed by combustion by introducing oxygen into the reaction system together with the starting compound, or by halting the reaction once and allowing oxygen or air to pass through the reaction tube.

There is no limitation to the pressure during the reaction insofar as the aforementioned starting compound and hydrogen fluoride can be present in a gaseous state. The reaction may be carried out under any pressure, i.e., normal pressure, increased pressure, or reduced pressure. Specifically, the preparation process of the present invention may be conducted under reduced pressure or atmospheric pressure (0.1 MPa), and may also be conducted under increased pressure so long as the starting material does not turn into a liquid state.

Although there is no particular limitation to the reaction time, the contact time determined by $V/F_o$ may be adjusted to a range of 0.1 to 100 sec, and preferably about 1 to 30 sec. $V/F_o$ is a ratio of a reaction space volume V (cc) in a gas phase to a total flow rate $F_0$ (flow rate at 0° C., 0.1 MPa: cc/sec) of starting material gases (starting compounds, hydrogen fluoride and an inert gas) introduced into the reaction system.

Under the above reaction conditions, a reaction product comprising $CF_3CCl=CH_2$ (2-chloro-3,3,3-trifluoropropene, HCFO-1233xf) can be obtained at the reactor outlet. HCFO-1233xf may be collected after being purified by distillation or other methods. The collected product may be used for a desired purpose as is, or may be converted into another compound.

In the production process of the present invention, the reaction product may contain, in addition to HCFO-1233xf, $CCl_2=CClCH_2Cl$ (HCO-1230xa), $CCl_3CCl=CH_2$(HCO-1230xf), $CFCl_2CHClCH_2Cl$ (HCFC-241db), $CFCl_2CCl=CH_2$(HCFO-1231xf), $CF_2ClCHClCH_2Cl$ (HCFC-242dc), $CF_2ClCCl=CH_2$(HCFO-1232xf), and the like. These compounds are produced as precursors of HCFO-1233xf, depending on the type of starting material used and the reaction conditions employed, and are all usable as a starting material in the preparation process of the present invention.

In the production process of the present invention, after HCFO-1233xf is isolated and collected, the above precursors contained in the reaction product and the unreacted starting materials, i.e., the chlorine-containing compounds represented by formulae (1), (2) and (3), may be returned to the reactor, so that they can be recycled and reused as starting materials. As described above, by recycling the precursors of HCFO-1233xf and the unreacted starting materials, even if the conversion rate of the starting materials is low, a high productivity can be maintained.

Advantageous Effects of Invention

The process of the present invention makes it possible to produce 2-chloro-3,3,3-trifluoropropene (HCFO-1233xf) with high selectivity by using a chlorine-containing compound represented by a specific formula as a starting material. According to the process of the present invention, 2-chloro-3,3,3-trifluoropropene (HCFO-1233xf) can be produced in a single step reaction at a remarkably high yield and relatively short contact time.

In particular, when the process of the present invention is performed in the absence of a catalyst, it eliminates all the defects that occur in known preparation processes utilizing catalysts. The target 2-chloro-3,3,3-trifluoropropene can be obtained with higher selectivity.

Further, the process of the present invention can be performed under mild conditions, i.e., normal pressure, reduced pressure, or the like, and it utilizes a gas phase reaction that is suitable for continuous preparation.

Therefore, the process of the present invention is highly advantageous for industrial application for producing 2-chloro-3,3,3-trifluoropropene (HCFO-1233xf).

DESCRIPTION OF EMBODIMENTS

Hereunder, the present invention is described in more detail with reference to Examples and Comparative Examples.

Comparative Example 1

A tubular reactor made of HASTELLOY®, having an inner diameter of 43 mm and a length of 50 cm, was packed with 2.3 kg of a plate made of HASTELLOY® (10 mm×20 mm×0.8 mm, hereunder this plate is referred to as a HASTELLOY plate). This reactor was maintained at atmospheric pressure (0.1 MPa) and a temperature of 400° C. Thereafter, nitrogen, an anhydrous hydrogen fluoride (HF) gas, and $CCl_3CHClCH_2Cl$ (HCC-240db) were respectively fed at a rate of 7.7 L/min (flow rate at 0° C. and 0.1 MPa), 7.5 L/min (flow rate at 0° C. and 0.1 MPa), and 0.68 L/min (gas flow rate at 0° C. and 0.1 MPa). Here, the amount of water supplied to the reactor was 40 ppm relative to the amount of HCC-240db. The molar ratio HF:HCC-240db was 11:1. The contact time ($V/F_0$) was calculated as 2.5 sec, based on the void volume of the HASTELLOY plate-packed bed (V=0.66 L) and the total flow rate of the materials supplied ($F_0$=15.9 L/min.). Eight hours later, the outlet gas from the reactor was analyzed using gas chromatography. Table 1 shows the analytical results.

Example 1

The reaction was performed in the same manner as in Comparative Example 1, except that $CCl_3CHClCH_2Cl$ (HCC-240db) saturated with water was used as the starting material. The amount of water supplied to the reactor was 200 ppm relative to the amount of HCC-240db. Table 1 shows the analytical data for the outlet gas.

Example 2

The reaction was performed under the same conditions as in Comparative Example 1, except that water was added from a line separate from the one for supplying the starting material in such a manner that the amount of water became 3,000 ppm relative to $CCl_3CHClCH_2Cl$ (HCC-240db). Table 1 shows the analytical data for the outlet gas.

The products obtained in this Example are shown below.
$CF_3CCl=CH_2$ (HCFO-1233xf)
$CF_2ClCCl=CH_2$ (HCFO-1232xf)
$CF_2ClCHClCH_2Cl$ (HCFC-242dc)

TABLE 1

|  | Comparative Example 1 | Example 1 | Example 2 |
| --- | --- | --- | --- |
| Water content (ppm) | 40 | 200 | 3000 |
| Conversion Rate of HCC-240db (%) | >99.99 | >99.99 | >99.99 |
| Selectivity of HCFO-1233xf (%) | 85.7 | 89.7 | 94.1 |
| Selectivity of HCFO-1232xf (%) | 4.9 | 2.4 | 1.2 |
| Selectivity of HCFC-242dc (%) | 6.6 | 6.0 | 2.7 |
| Other Selectivity (%) | 2.8 | 1.9 | 2.0 |

Comparative Example 2

A tubular reactor made of HASTELLOY®, having an inner diameter of 43 mm and a length of 50 cm, was packed with 2.3 kg of a HASTELLOY plate (10 mm×20 mm×0.8 mm). This reactor was maintained at atmospheric pressure (0.1 MPa) and a temperature of 400° C. Thereafter, nitrogen, an anhydrous hydrogen fluoride (HF) gas, and $CCl_3CHClCH_2Cl$ (HCC-240db) were supplied at a rate of 5.0 L/min (flow rate at 0° C. and 0.1 MPa), 10.2 L/min (flow rate at 0° C. and 0.1 MPa), and 0.68 L/min (gas flow rate at 0° C. and 0.1 MPa), respectively. Here, the amount of water supplied to the reactor was 40 ppm relative to the amount of HCC-240db. The molar ratio HF:HCC-240db was 15:1. The contact time ($V/F_0$) was calculated as 2.5 sec, based on the void volume of the HASTELLOY plate-packed bed (V=0.66 L) and the total flow rate of the materials supplied ($F_0$=15.9 L/min.). Eight hours later, the outlet gas from the reactor was analyzed using gas chromatography. Table 2 shows the analytical results.

Example 3

The reaction was performed in the same manner as in Comparative Example 2, except that $CCl_3CHClCH_2Cl$ (HCC-240db) saturated with water was used as the starting material. The amount of water supplied to the reactor was 200 ppm relative to the amount of HCC-240db. Table 2 shows the analytical data for the outlet gas.

Example 4

The reaction was performed under the same conditions as in Comparative Example 2, except that water was added from a line separate from the one for supplying the starting material in such a manner that the amount of water supplied became 3,000 ppm relative to the amount of $CCl_3CHClCH_2Cl$ (HCC-240db). Table 2 shows the analytical data for the outlet gas.

TABLE 2

|  | Comparative Example 2 | Example 3 | Example 4 |
| --- | --- | --- | --- |
| Water content (ppm) | 40 | 200 | 3000 |
| Conversion Rate of HCC-240db (%) | >99.99 | >99.99 | >99.99 |
| Selectivity of HCFO-1233xf (%) | 91.2 | 93.5 | 94.3 |
| Selectivity of HCFO-1232xf (%) | 0.3 | 0.2 | 0.3 |
| Selectivity of HCFC-242dc (%) | 6.3 | 4.5 | 3.5 |
| Other Selectivity (%) | 2.2 | 1.8 | 1.9 |

Comparative Example 3

A tubular reactor made of HASTELLOY®, having an inner diameter of 43 mm and a length of 50 cm, was packed with 2.3 kg of a HASTELLOY plate (10 mm×20 mm×0.8 mm). This reactor was maintained at atmospheric pressure (0.1 MPa) and a temperature of 400° C. Thereafter, nitrogen, an anhydrous hydrogen fluoride (HF) gas, and $CCl_3CHClCH_2Cl$ (HCC-240db) were supplied at a rate of 0.7 L/min (flow rate at 0° C. and 0.1 MPa), 14.4 L/min (flow rate at 0° C. and 0.1 MPa), and 0.68 L/min (gas flow rate at 0° C. and 0.1 MPa), respectively. Here, the amount of water supplied to the reactor was 40 ppm relative to the amount of HCC-240db. The molar ratio HF:HCC-240db was 21:1. The contact time ($V/F_0$) was calculated as 2.5 sec, based on the void volume of the HASTELLOY plate-packed bed (V=0.66 L) and the total flow rate of the materials supplied ($F_0$=15.9 L/min). Eight hours later, the outlet gas from the reactor was analyzed using gas chromatography. Table 3 shows the analytical results.

Example 5

The reaction was performed in the same manner as in Comparative Example 3, except that $CCl_3CHClCH_2Cl$ (HCC-240db) saturated with water was used as the starting material. The amount of water supplied to the reactor was 200 ppm relative to the amount of HCC-240db. Table 3 shows the analytical data for the outlet gas.

Example 6

The reaction was performed under the same conditions as in Comparative Example 3, except that water was added from a line separate from the one for supplying the starting material in such a manner that the amount of water supplied became 3,000 ppm relative to the amount of $CCl_3CHClCH_2Cl$ (HCC-240db). Table 3 shows the analytical data for the outlet gas.

TABLE 3

|  | Comparative Example 3 | Example 5 | Example 6 |
| --- | --- | --- | --- |
| Water content (ppm) | 40 | 200 | 3000 |
| Conversion Rate of HCC-240db (%) | >99.99 | >99.99 | >99.99 |
| Selectivity of HCFO-1233xf (%) | 89.2 | 92.3 | 93.5 |
| Selectivity of HCFO-1232xf (%) | 0.4 | 0.5 | 0.2 |
| Selectivity of HCFC-242dc (%) | 7.9 | 4.9 | 3.5 |
| Other Selectivity (%) | 2.5 | 2.3 | 2.8 |

The invention claimed is:

1. A process for preparing 2-chloro-3,3,3-trifluoropropene comprising:
    reacting a chlorine-containing compound with anhydrous hydrogen fluoride while being heated in a gaseous state in the presence of 50 ppm or more of water relative to the total weight of the chlorine-containing compound,
    the chlorine-containing compound being at least one compound selected from the group consisting of chloropropane represented by formula (1): $CX_3CHClCH_2Cl$, wherein each X is the same or different and each represents Cl or F; chloropropene represented by formula (2): $CClY_2CCl\!=\!CH_2$, wherein each Y is the same or different and each represents Cl or F; and chloropropene represented by formula (3): $CZ_2\!=\!CClCH_2Cl$, wherein each Z is the same or different and each represents Cl or F.

2. The process according to claim 1, wherein the reaction is conducted in the absence of a catalyst.

3. The process for preparing 2-chloro-3,3,3-trifluoropropene according to claim 1, wherein the hydrogen fluoride is used in an amount of 5 to 30 mol relative to 1 mol of the chlorine-containing compound used as a starting material, and the reaction is carried out at 300° C. to 500° C.

4. The process for preparing 2-chloro-3,3,3-trifluoropropene according to claim 2, wherein the hydrogen fluoride is used in an amount of 5 to 30 mol relative to 1 mol of the chlorine-containing compound used as a starting material, and the reaction is carried out at 300° C. to 500° C.

* * * * *